(12) United States Patent
Kimura et al.

(10) Patent No.: US 11,718,837 B2
(45) Date of Patent: Aug. 8, 2023

(54) LIPASE AND USES OF THE SAME

(71) Applicant: AMANO ENZYME INC., Nagoya (JP)

(72) Inventors: Tomohiro Kimura, Kakamigahara (JP); Tomoya Ryoki, Kakamigahara (JP); Yusuke Tanaka, Kakamigahara (JP); Naoto Katsumata, Kakamigahara (JP); Yukihide Sato, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 2 days.

(21) Appl. No.: 17/255,831

(22) PCT Filed: Jul. 29, 2020

(86) PCT No.: PCT/JP2020/029104
§ 371 (c)(1),
(2) Date: Dec. 23, 2020

(87) PCT Pub. No.: WO2021/020458
PCT Pub. Date: Feb. 4, 2021

(65) Prior Publication Data
US 2021/0214696 A1 Jul. 15, 2021

(30) Foreign Application Priority Data
Aug. 1, 2019 (JP) ................. 2019-142145

(51) Int. Cl.
*C12N 9/20* (2006.01)
*C12P 7/64* (2022.01)
*C12P 7/6454* (2022.01)

(52) U.S. Cl.
CPC .......... *C12N 9/20* (2013.01); *C12P 7/64* (2013.01); *C12P 7/6454* (2013.01); *C12Y 301/01003* (2013.01)

(58) Field of Classification Search
CPC ... C12P 7/6454; C12P 7/64; C12Y 301/01003
See application file for complete search history.

(56) References Cited

U.S. PATENT DOCUMENTS

| 7,648,724 B2 | 1/2010 | Arimoto et al. |
| 2007/0231446 A1 | 10/2007 | Nagasawa et al. |
| 2011/0117616 A1 | 5/2011 | Hatakeyama et al. |

FOREIGN PATENT DOCUMENTS

| JP | H02-504342 A | 12/1990 |
| JP | H06-153965 A | 6/1994 |
| JP | H08-256767 A | 10/1996 |
| JP | H10-215888 A | 8/1998 |
| JP | H11-253157 A | 9/1999 |
| JP | 3791943 B2 | 6/2006 |
| JP | 2007-099871 A | 4/2007 |
| JP | 2008-194011 A | 8/2008 |
| JP | 2009-138185 A | 6/2009 |
| WO | 89/01032 A1 | 2/1989 |
| WO | 2006/059592 A1 | 6/2006 |
| WO | 2006/121182 A1 | 11/2006 |
| WO | 2010/005003 A1 | 1/2010 |
| WO | 2013/146529 A1 | 10/2013 |
| WO | 2018/021324 A1 | 2/2018 |

OTHER PUBLICATIONS

Written Opinion—PCT/JP2020/029104 (Year: 2020).*
Yang et al. [Journal of Molecular Catalysis B: Enzymatic (2016), 126, 76-89]. (Year: 2016).*
Matsumoto, W. "Interesterificaion of Fats and Oils," Journal of Japan Oil Chemists' Society, 48, 1999, pp. 1151-1159 (discussed in the spec).
Nezu T. et al., "Recent Development of Fat Modification Process," Oleoscience, 6, 2006, pp. 145-151. (discussed in the spec).
Macrae, A.R., "Lipase-Catalysed Interesterification of Oils and Fats," J. Am. Oil Chem. Soc., 1983, vol. 60, No. 2, pp. 291-294. (discussed in the spec).
Lai, O. M. "Physical Properties of Pseudomonas and Rhizomucor miehei Lipase-Catalyzed Transesterified Blends of Palm Stearin: Palm Kernel Olein," J. Am. Oil Chem. Soc., 75, 1998, pp. 953-959. (discussed in the spec).
Jorgensen, S. et al., "Cloning, Sequence, and Expression of a Lipase Gene from Pseudomonas cepacia: Lipase Production in Heterologous Hosts Requires Two Pseudomonas Genes," J. Bacteriol., 1991, vol. 173. No. 2, pp. 559-567. (cited in the ISR).
Yang, W. et al., "A new extracellular thereto-solvent-stable lipase from Burkholderia ubonensis SL-4: Identification, characterization and application for biodiesel production," J. Mol. Catal. B. Enzym., 2016, vol. 126, pp. 76-89, (cited in the ISR).
Sanchez, D.A. et al., "Screening of Lipases with Unusual High Activity in the sn-2 Esterification of 1,3-Dicaprin under Mild Operating Conditions," J. Agri. Food Chem., 2017, vol. 65. pp. 5010-5017. (cited in the ISR).
Lu, Y. et al., "Identification of bacteria producing a thermophilie lipase with positional non-specificity and characterization of the lipase," Ann Microbiol., 2009, vol. 59, No. 3, pp. 565-571. (cited in the ISR).
Yao, C. et al., "An organic solvent and thermally stable lipase from Burkholderia ambifaria YCJ01: Purification, characteristics and application for chiral resolution of mandelic acid," J. Mol. Catal. B, Enzym., 2013, vol. 85-86, pp. 105-110. (cited in the ISR).
Mak, A. et al., "Preclinical safety evaluation of triacylglycerol lipase QLM from Burkholderia ubonensis," Regul. Toxicol. and Pharnacol., Nov. 11, 2019, vol. 110, Article No. 104523, pp. 1-11. (cited in the ISR).

(Continued)

*Primary Examiner* — Tekchand Saidha
(74) *Attorney, Agent, or Firm* — Locke Lord LLP (57) ABSTRACT

To find a novel lipase suitable for processing of oils and fats and to use and apply the lipase. Provided are a novel lipase including an amino acid sequence having 90% or more identity with an amino acid sequence of SEQ ID NO: 1 or 2, and an enzyme preparation containing the same as an active ingredient. The enzyme preparation is used for modifying and improving the physical properties of oils and fats.

8 Claims, 5 Drawing Sheets
Specification includes a Sequence Listing.

(56) References Cited

OTHER PUBLICATIONS

Lai, O. M. et al., "Effect of Enzymatic Transesterification on the Melting Points of Palm Stearin-Sunflower Oil Mixtures," J. Am, Oil Chem. Soc, 1998, vol. 75, No. 7, pp. 881-886. (cited in the ISR).
Sato, Y. "About Characteristics and Effectiveness of Lipase" Wakojunyaku Jiho, vol. 84, No. 3, 2016, pp. 11-13. (cited in the ISR).
International Search Report dated Sep. 8, 2020, issued for PCT/JP20020/029104.
Supplementary European Search Report dated Jan. 25, 2022, issued for European Patent Application No. 20829174.0.
Yang Wenjuan et al., "A new extracellular thermo-solvent-stable lipase from Burkholderia ubonensis SL-4: Identification, characterization and application for biodiesel production", Journal of Molecular Catalysis B : Enzymatic, vol. 126, Feb. 11, 2016, pp. 76-89. (cited in the Jan. 25, 2022 Search Report issued for EP20829174.0).
Database UniProt [Online], Mar. 16, 2016, "Lipase from Burkholderia ubonensis; EC=3.1.1.3", XP002805227, retrieved from EBI accession No. Uniprot:A0A0U2QQQ4, Database accession No. A0A0U2QQQ4. (cited in the Jan. 25, 2022 Search Report issued for EP20829174.0).
Database Uniparc [Online] Nov. 23, 2018, "Alpha/beta hydrolase from Burkholderia ubonensis", XP002805228, Database accession No. UPI000F6FFC8E. (cited in the Jan. 25, 2022 Search Report issued for EP20829174.0).
Database GenPept [Online], Apr. 24, 2018, "Triacylglycerol lipase [Burkholderia ubonensis]", XP002805229, Database accession No. WP_059870359. (cited in the Jan. 25, 2022 Search Report issued for EP20829174.0).
Dang-Thuan Tran et al., "Kinetics of enzymatic transesterification and thermal deactivation using immobilized Burkholderia lipase as catalyst", Bioprocess and Biosystems Engineering, Springer, DE, vol. 37, No. 3, Jul. 24, 2013, pp. 481-491. (cited in the Jan. 25, 2022 Search Report issued for EP20829174.0).
Alastair Mak et al., "Preclinical safety evaluation of triacylglycerol lipase QLM from Burkholderia ubonensis," Regulatory Toxicology and Pharmacology 110, 2020, 104523, pp. 1-11. (cited in the Sep. 22, 2021 Notice of Opposition).
triacylglycerol lipase [Burkholderia ubonensis], NCBI Reference Sequence: WP_059870359.1, Aug. 19, 2021,1 page, (cited in the Sep. 22, 2021 Notice of Opposition).
WP 059870359.1 triacylglycerol lipase [Burkholderia ubonensis]. . . NCBI Blast:WP_059870359.1, Aug. 31, 2021,4 pages, (cited in the Sep. 22, 2021 Notice of Opposition).
Wenjuan Yang et al., "A new extracellular thermo-solvent-stable lipase from Burkholderia ubonensis SL-4: Identification, characterization and application for biodiesel production," Journal of Molecular Catalysis B: Enzymatic 126, 2016, pp. 76-89. (cited in the Sep. 22, 2021 Notice of Opposition).
B. ubonensis SL-4 Lipase (Full), NCBI Blast:B. ubonensis SL-4 Lipase (Full), Sep. 14, 2021, 4 pages, (cited in the Sep. 22, 2021 Notice of Opposition).
Y. Shimada et al., "Advanced processing of highly unsaturated fatty acid-containing oil using lipase (Part 1)," Yushi, vol. 50, No. 12, 1997, pp. 66-70, information sheets and its partial English translation, (cited in the Sep. 22, 2021 Notice of Opposition).
"Functions of lipase and food correspondence," Food—its science and technology, No. 45, NARO, Mar. 1, 2007, pp. 1-18, information sheet and its partial English translation, (cited in the Sep. 22, 2021 Notice of Opposition).
In-Hwan Kim et al., "Lipase-Catalyzed Incorporation of Conjugated Linoleic Acid into Tricaprylin," JAOCS, vol. 78, No. 5, 2001, pp. 547-551 and Abstract, (cited in the Sep. 22, 2021 Notice of Opposition).
H. Noureddini et al., "Immobilized Pseudomonas cepacia lipase for biodiesel fuel production from soybean oil," Bioresource Technology 96 (2005) pp. 769-777. (cited in the Sep. 22, 2021 Notice of Opposition).
"Application of Burkholderia cepacia to agricultural products and its effect on humans," IASR, CDC, EID, 4 No. 2 221, 1998, 1 page and machine English translation thereof (cited in the Dec. 21, 2021 Office Action issued for JP6846577).
"CAS RN: 538-23-8, Product Code: T0365," Trycaprylin 538-23-8, Tokyo Kasei Kogyo Kabushiki Kaisha, 7 pages and English translation thereof (cited in the Dec. 21, 2021 Office Action issued for JP6846577).
Office action after post-grant opposition dated Dec. 21, 2021, issued for Japanese Patent No. 6846577 and a partial English translation thereof.

\* cited by examiner

```
                        SEQUENCE LISTING

<160> NUMBER OF SEQ ID NOS: 4

<210> SEQ ID NO 1
<211> LENGTH: 364
<212> TYPE: PRT
<213> ORGANISM: Burkholderia ubonensis

<400> SEQUENCE: 1

Met Ala Arg Ser Met Arg Ser Arg Val Val Ala Gly Ala Val Ala Cys
1               5                   10                  15

Ala Met Ser Ala Ala Pro Phe Ala Gly Met Thr Ala Leu Ala Thr Val
            20                  25                  30

Ala Thr Thr Arg Ala Ala Val Ala

|   |   |
|---|---|
| 355 | 360 |

<210> SEQ ID NO 2
<211> LENGTH: 320
<212> TYPE: PRT
<213> ORGANISM: Burkholderia ubonensis

<400> SEQUENCE: 2

| Ala | Asp | Asp | Tyr | Ala | Thr | Thr | Arg | Tyr | Pro | Ile | Ile | Leu | Val | His | Gly |
|---|---|---|---|---|---|---|---|---|---|---|---|---|---|---|---|
| 1 | | | | 5 | | | | | 10 | | | | | 15 | |

| Leu | Thr | Gly | Thr | Asp | Lys | Tyr | Ala | Gly | Val | Leu | Asp | Tyr | Phe | Tyr | Gly |
|---|---|---|---|---|---|---|---|---|---|---|---|---|---|---|---|
| | | | 20 | | | | | 25 | | | | | 30 | | |

| Ile | Gln | Gln | Asp | Leu | Gln | Gln | His | Gly | Ala | Thr | Val | Tyr | Val | Ala | Asn |
|---|---|---|---|---|---|---|---|---|---|---|---|---|---|---|---|
| | | | 35 | | | | | 40 | | | | | 45 | | |

| Leu | Ser | Gly | Tyr | Gln | Ser | Asp | Asp | Gly | Pro | Asn | Gly | Arg | Gly | Glu | Gln |
|---|---|---|---|---|---|---|---|---|---|---|---|---|---|---|---|
| | 50 | | | | | 55 | | | | | 60 | | | | |

| Leu | Leu | Ala | Gln | Val | Lys | Gln | Val | Leu | Ala | Gln | Thr | Gly | Ala | Ala | Lys |
|---|---|---|---|---|---|---|---|---|---|---|---|---|---|---|---|
| 65 | | | | | 70 | | | | | 75 | | | | | 80 |

| Val | Asn | Leu | Ile | Gly | His | Ser | Gln | Gly | Gly | Leu | Ser | Ser | Arg | Tyr | Val |
|---|---|---|---|---|---|---|---|---|---|---|---|---|---|---|---|
| | | | | 85 | | | | | 90 | | | | | 95 | |

| Ala | Ala | Val | Ala | Pro | Glu | Leu | Val | Ala | Ser | Val | Thr | Thr | Ile | Gly | Thr |
|---|---|---|---|---|---|---|---|---|---|---|---|---|---|---|---|
| | | | 100 | | | | | 105 | | | | | 110 | | |

| Pro | His | Arg | Gly | Ser | Glu | Phe | Ala | Asp | Phe | Val | Gln | Gly | Val | Leu | Ala |
|---|---|---|---|---|---|---|---|---|---|---|---|---|---|---|---|
| | | 115 | | | | | 120 | | | | | 125 | | | |

| Tyr | Asp | Pro | Thr | Gly | Leu | Ser | Ser | Thr | Val | Ile | Ala | Ala | Phe | Val | Asn |
|---|---|---|---|---|---|---|---|---|---|---|---|---|---|---|---|
| 130 | | | | | 135 | | | | | 140 | | | | | |

| Val | Phe | Gly | Met | Leu | Thr | Ser | Ser | Thr | His | Asn | Thr | Asn | Gln | Asp | Ala |
|---|---|---|---|---|---|---|---|---|---|---|---|---|---|---|---|
| 145 | | | | | 150 | | | | | 155 | | | | | 160 |

| Leu | Ala | Ala | Leu | Gln | Thr | Leu | Thr | Thr | Ala | Arg | Ala | Ala | Thr | Tyr | Asn |
|---|---|---|---|---|---|---|---|---|---|---|---|---|---|---|---|
| | | | | 165 | | | | | 170 | | | | | 175 | |

| Gln | Asn | Phe | Pro | Ser | Ala | Gly | Leu | Gly | Ala | Pro | Gly | Ser | Cys | Gln | Ser |
|---|---|---|---|---|---|---|---|---|---|---|---|---|---|---|---|
| | | | 180 | | | | | 185 | | | | | 190 | | |

| Gly | Ala | Pro | Thr | Glu | Thr | Val | Gly | Gly | Asn | Thr | His | Leu | Leu | Tyr | Ser |
|---|---|---|---|---|---|---|---|---|---|---|---|---|---|---|---|
| | | 195 | | | | | 200 | | | | | 205 | | | |

| Trp | Ala | Gly | Thr | Ala | Ile | Gln | Pro | Thr | Phe | Ser | Ala | Leu | Gly | Val | Thr |
|---|---|---|---|---|---|---|---|---|---|---|---|---|---|---|---|
| 210 | | | | | 215 | | | | | 220 | | | | | |

| Gly | Ala | Lys | Asp | Thr | Ser | Thr | Ile | Pro | Val | Val | Asp | Pro | Ala | Asn | Ala |
|---|---|---|---|---|---|---|---|---|---|---|---|---|---|---|---|
| 225 | | | | | 230 | | | | | 235 | | | | | 240 |

| Leu | Asp | Ala | Ser | Thr | Leu | Ala | Leu | Leu | Gly | Ser | Gly | Thr | Val | Met | Ile |
|---|---|---|---|---|---|---|---|---|---|---|---|---|---|---|---|
| | | | | 245 | | | | | 250 | | | | | 255 | |

| Asn | Arg | Gly | Ser | Gly | Glu | Asn | Asp | Gly | Val | Val | Ser | Lys | Cys | Ser | Ala |
|---|---|---|---|---|---|---|---|---|---|---|---|---|---|---|---|
| | | | 260 | | | | | 265 | | | | | 270 | | |

| Leu | Phe | Gly | Gln | Val | Leu | Ser | Thr | Ser | Tyr | Lys | Trp | Asn | His | Val | Asp |
|---|---|---|---|---|---|---|---|---|---|---|---|---|---|---|---|
| | | 275 | | | | | 280 | | | | | 285 | | | |

| Glu | Ile | Asn | Gln | Leu | Leu | Gly | Val | Arg | Gly | Ala | Tyr | Ala | Glu | Asp | Pro |
|---|---|---|---|---|---|---|---|---|---|---|---|---|---|---|---|
| 290 | | | | | 295 | | | | | 300 | | | | | |

| Val | Ala | Val | Ile | Arg | Thr | His | Ala | Asn | Arg | Leu | Lys | Leu | Ala | Gly | Val |
|---|---|---|---|---|---|---|---|---|---|---|---|---|---|---|---|
| 305 | | | | | 310 | | | | | 315 | | | | | 320 |

<210> SEQ ID NO 3
<211> LENGTH: 1095
<212> TYPE: DNA
<213> ORGANISM: Burkholderia ubonensis

<400> SEQUENCE: 3

```
atggccagat caatgcgttc cagggtggtg gcaggggcag tggcatgcgc gatgagcgcc      60
```

-continued

```
gcgccgttcg cgggcatgac cgcgctcgcg acggttgcga cgacgcgcgc ggcggtggcg 120
gcaaccgcac cggccgacga ttacgcgacg acgcgttatc cgatcattct cgtgcacggg 180
ctgacgggca ccgacaagta tgcgggcgtg ctcgattact tttacggcat ccagcaggac 240
ctgcagcagc atggcgcgac cgtgtacgtc gcgaacctgt ccggctacca gagcgacgac 300
ggcccgaacg ggcgcggcga gcaattgctc gcgcaagtga agcaggtgct tgcgcagacc 360
ggcgcggcca aggtcaacct gatcggccac agccagggcg gcctgtcgtc gcgctatgtc 420
gccgccgtcg cgccggagct ggtcgcgtcg gtgacgacga tcggcacgcc gcaccgcggc 480
tcggaattcg cggacttcgt gcagggcgtg ctcgcgtacg acccgaccgg tctttcgtcg 540
acagtgatcg cggcgttcgt caatgtgttc ggcatgctga cgagcagcac ccacaacacc 600
aaccaggacg cgctcgccgc gctgcagacg ctgaccacgg cgcgggccgc gacctataac 660
cagaacttcc cgagcgcggg gctcggcgcg cccggctcgt gccagagcgg cgcgccgacg 720
gagacggtcg gcggcaacac gcacctgctg tactcgtggg ccggcaccgc gatccagccg 780
acgttctccg cgctgggcgt gacgggcgcg aaggatacga gcacgatccc ggtcgtcgat 840
ccggcgaatg cgctcgacgc gtcgacgctc gcgctgctcg gcagcggcac ggtgatgatc 900
aaccgcggct cgggcgaaaa cgacggcgtc gtgtcgaaat gcagcgcgct gttcgggcag 960
gtgctgagca cgagctacaa gtggaaccac gtcgacgaga tcaaccagct gctgggcgtg 1020
cgcggcgcgt atgcggaaga cccggtcgcg gtgatccgca cgcacgcgaa ccggctgaag 1080
ctcgcgggcg tgtaa 1095

<210> SEQ ID NO 4
<211> LENGTH: 963
<212> TYPE: DNA
<213> ORGANISM: Burkholderia ubonensis
<400> SEQUENCE: 4
gccgacgatt acgcgacgac gcgttatccg atcattctcg tgcacgggct gacgggcacc 60
gacaagtatg cgggcgtgct cgattacttt tacggcatcc agcaggacct gcagcagcat 120
ggcgcgaccg tgtacgtcgc gaacctgtcc ggctaccaga gcgacgacgg cccgaacggg 180
cgcggcgagc aattgctcgc gcaagtgaag caggtgcttg cgcagaccgg cgcggccaag 240
gtcaacctga tcggccacag ccagggcggc ctgtcgtcgc gctatgtcgc cgccgtcgcg 300
ccggagctgg tcgcgtcggt gacgacgatc ggcacgccgc accgcggctc ggaattcgcg 360
gacttcgtgc agggcgtgct cgcgtacgac ccgaccggtc tttcgtcgac agtgatcgcg 420
gcgttcgtca atgtgttcgg catgctgacg agcagcaccc acaacaccaa ccaggacgcg 480
ctcgccgcgc tgcagacgct gaccacggcg cgggccgcga cctataacca gaacttcccg 540
agcgcggggc tcggcgcgcc cggctcgtgc cagagcggcg cgccgacgga gacggtcggc 600
ggcaacacgc acctgctgta ctcgtgggcc ggcaccgcga tccagccgac gttctccgcg 660
ctgggcgtga cgggcgcgaa ggatacgagc acgatcccgg tcgtcgatcc ggcgaatgcg 720
ctcgacgcgt cgacgctcgc gctgctcggc agcggcacgg tgatgatcaa ccgcggctcg 780
ggcgaaaacg acggcgtcgt gtcgaaatgc agcgcgctgt tcgggcaggt gctgagcacg 840
agctacaagt ggaaccacgt cgacgagatc aaccagctgc tgggcgtgcg cggcgcgtat 900
gcggaagacc cggtcgcggt gatccgcacg cacgcgaacc ggctgaagct cgcgggcgtg 960
taa 963

LIPASE AND USES OF THE SAME

TECHNICAL FIELD

The present invention relates to a novel lipase having a transesterification ability and uses of the same. The present application claims priority based on Japanese Patent Application No. 2019-142145 filed on Aug. 1, 2019, the entire contents of which are incorporated herein by reference.

BACKGROUND ART

Transesterification reactions of oils and fats are effective methods for modifying the physical properties of oils and fats (melting point, crystallinity, heat resistance, etc.), and are roughly classified into two groups, chemical transesterification and enzymatic transesterification (see, for example, NPLs 1 and 2). The chemical transesterification has many problems such as high environmental load and poor work safety. In recent years, due to concern about the health risk of trans-fatty acids, attention has been paid to the manufacture of transesterified oils and fats as an alternative to partial hydrogenation that causes the production of trans-fatty acids. It is said that, for the enzymatic transesterification, lipases derived from the genera *Candida, Alcaligenes, Pseudomonas, Thermomyces, Burkholderia*, and the like can be used (see, for example, PTLs 1 to 4 and NPLs 3 and 4).

CITATION LIST

Patent Literature

[PTL 1] WO 2006/059592
[PTL 2] JP 3791943 B
[PTL 3] JP 2008-194011 A
[PTL 4] JP 1102-504342 A

Non Patent Literature

[NPL 1] Journal of Japan Oil Chemists' Society, 48, 1151-1159 (1999)
[NPL 2] Oleoscience, 6, 145-151 (2006)
[NPL 3] J. Am. Oil Chem. Soc., 60, 291-294 (1983)
[NPL 4] J. Am. Oil Chem. Soc., 75, 953-959 (1998)

SUMMARY OF INVENTION

Technical Problem

In processing of oils and fats, the need for enzymatic transesterification is high. However, an enzyme that has a high transesterification ability and is less likely to cause a hydrolysis reaction, which is a side reaction, during the reaction has not been put into practical use. The occurrence of hydrolysis during the transesterification reaction reduces the yield of oils and fats or triglycerides, resulting in the production of partial glycerides (diglycerides and monoglycerides) and fatty acids which adversely affect the quality of oils and fats. In order to overcome this actual situation, an object of the present invention is to find an enzyme (transesterification lipase) that is unlikely to cause a hydrolysis reaction, which is a side reaction, during the transesterification reaction, and to use and apply the enzyme.

Solution to Problem

In order to find a transesterification lipase suitable for processing of oils and fats, the present inventors searched among various microorganism-derived lipases. As a result, a novel lipase having an excellent transesterification ability (the present lipase) was found. That is, the present inventors have succeeded in obtaining and identifying a transesterification lipase that has high industrial utility. Furthermore, the present inventors have succeeded in identifying the amino acid sequences of the enzyme and the base sequences of a gene encoding the enzyme.

Based on the above results and consideration, the following inventions are provided.

[1] A lipase including an amino acid sequence having 90% or more identity with an amino acid sequence of SEQ ID NO: 1 or 2.

[2] The lipase according to [1], wherein the amino acid sequence of the lipase is an amino acid sequence exhibiting 93% or more identity with the amino acid sequence shown in SEQ ID NO: 1 or 2.

[3] The lipase according to [1], wherein the amino acid sequence of the lipase is an amino acid sequence exhibiting 95% or more identity with the amino acid sequence shown in SEQ ID NO: 1 or 2.

[4] An enzyme preparation including the lipase according to any one of [1] to [3] as an active ingredient.

[5] A method for manufacturing a lipase, including the following steps (1) and (2):
(1) culturing a producer microorganism for the lipase according to any one of [1] to [3]; and
(2) collecting the lipase from a culture solution and/or cell bodies after the culture.

[6] A method for manufacturing an oil or fat, including an enzymatic reaction with the lipase according to any one of [1] to [3] or the enzyme preparation according to [4] in the presence of an acceptor substrate and a donor substrate.

[7] The manufacture method according to [6],
wherein the acceptor substrate is an oil or fat, glycerin fatty acid ester, or glycerin, and
wherein the donor substrate is a fatty acid, an ester compound, or an oil or fat.

DESCRIPTION OF EMBODIMENTS

1. Transesterification Lipase Preparation and Active Ingredient Thereof (Transesterification Lipase)

The present invention relates to an enzyme preparation (transesterification lipase preparation) useful for transesterification of oils and fats. The enzyme preparation of the present invention (hereinafter, referred to also as "the present enzyme preparation") contains a transesterification lipase (hereinafter referred to also as "the present enzyme") as an active ingredient. The active ingredient transesterification lipase, that is, the present enzyme, includes an amino acid sequence shown in SEQ ID NO: 1 or 2, or an amino acid sequence equivalent to the amino acid sequence. The "equivalent amino acid sequence" herein refers to an amino acid sequence which is partially different from the reference amino acid sequence (amino acid sequence of SEQ ID NO: 1 or amino acid sequence of SEQ ID NO: 2), but in which the difference does not substantially affect the function (herein, transesterification ability) of the protein. Thus, an enzyme having the equivalent amino acid sequence catalyzes a transesterification reaction. The degree of activity is not particularly limited as long as the function as a transesterification lipase can be exerted. However, it is preferable that the activity be equivalent to or higher than that of the enzyme including the reference amino acid sequence.

The amino acid sequence of SEQ ID NO: 1 is an amino acid sequence including a signal peptide sequence of the transesterification lipase, and SEQ ID NO: 2 is an amino acid sequence obtained by excluding the signal peptide sequence from SEQ ID NO: 1 (amino acid sequence of mature form).

The "partial difference in amino acid sequence" is caused, for example, by deletion or substitution of one or more amino acids in the amino acids constituting the amino acid sequence, addition or insertion of one or more amino acids to/into the amino acid sequence, or any combination thereof. The partial difference in amino acid sequence is allowed as long as the transesterification activity is retained (the activity may slightly vary). The position where the difference in amino acid sequence is present is not particularly limited as long as this condition is satisfied. Further, the difference in amino acid sequence may occur at a plurality of places (locations).

The number of amino acids that cause the partial difference in amino acid sequence is, for example, a number corresponding to less than about 30%, preferably a number corresponding to less than about 20%, more preferably a number corresponding to less than about 15%, further preferably a number corresponding to less than about 10%, even further preferably a number corresponding to less than about 7%, still even further preferably less than about 5%, further more preferably a number corresponding to less than about 3%, still further more preferably less than about 2%, most preferably less than about 1%, of all the amino acids constituting the amino acid sequence. Therefore, the equivalent protein has, for example, about 70% or more, preferably about 80% or more, more preferably about 85% or more, further preferably about 90% or more, even further preferably about 93% or more, still even further preferably about 95% or more, further more preferably about 97% or more, still further more preferably about 98% or more, most preferably about 99% or more identity with the reference amino acid sequence.

A typical example of the "partial difference in amino acid sequence" is a mutation (change) of the amino acid sequence caused by deletion or substitution of 1 to 40 (preferably 1 to 30, more preferably 1 to 10, further preferably 1 to 7, even further preferably 1 to 5, still further preferably 1 to 3) amino acids among the amino acids constituting the amino acid sequence; addition or insertion of 1 to 40 (preferably 1 to 30, more preferably 1 to 10, further preferably 1 to 7, even further preferably 1 to 5, further more preferably 1 to 3) amino acids to/into the amino acid sequence; or a combination thereof.

Preferably, conservative amino acid substitution occurs at amino acid residues that are not essential for a transesterification ability to obtain an equivalent amino acid sequence. The term "conservative amino acid substitution" as used herein refers to substitution of an amino acid residue with an amino acid residue having a side chain with similar properties. Amino acid residues are classified into several families depending on their side chains: a basic side chain (for example, lysine, arginine, and histidine); an acidic side chain (for example, aspartic acid and glutamic acid); an uncharged polar side chain (for example, glycine, asparagine, glutamine, serine, threonine, tyrosine, and cysteine); a non-polar side chain (for example, alanine, valine, leucine, isoleucine, proline, phenylalanine, methionine, and tryptophan); a beta-branched side chain (for example, threonine, valine, and isoleucine); and an aromatic side chain (for example, tyrosine, phenylalanine, tryptophan, and histidine). The conservative amino acid substitution is preferably substitution between amino acid residues within the same family. Since the active residues of the lipase (SEQ ID NO: 2) of the present invention are presumed to be the amino acid serine at position 87, the amino acid aspartic acid at position 264, and the amino acid histidine at position 286, it is preferred that substitution have occurred in an amino acid residue other than the amino acid residues.

The identity (%) between two amino acid sequences can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

Comparison between two sequences and determination of identity thereof can be realized using a mathematical algorithm. A specific example of the mathematical algorithm that can be used for comparison between sequences is the algorithm described in Karlin and Altschul (1990) Proc. Natl. Acad. Sci. USA 87: 2264-68 and modified in Karlin and Altschul (1993) Proc. Natl. Acad. Sci. USA 90: 5873-77, but the mathematical algorithm is not limited thereto. Such an algorithm is incorporated into the NBLAST program and XBLAST program (version 2.0) described in Altschul et al. (1990) J. Mol. Biol. 215:403-10. BLAST polypeptide search may be carried out using the XBLAST program, under the settings: score=50 and wordlength=3, to obtain an amino acid sequence equivalent to the reference amino acid sequence. Gapped BLAST as described in Altschul et al. (1997) Amino Acids Research 25(17):3389-3402 can be utilized to obtain gap alignments for comparison. When BLAST and Gapped BLAST are utilized, the default parameters of the corresponding programs (e.g., XBLAST and NBLAST) can be used. For more information, see http://www.ncbi.nlm.nih.gov. Examples of other mathematical algorithms that can be used for comparison between sequences include the algorithm described in Myers and Miller (1988) Comput Appl Biosci. 4:11-17. Such an algorithm is, for example, incorporated in the ALIGN program available on the GENESTREAM network server (IGH Montpellier, France) or the ISREC server. When the ALIGN program is utilized for comparison between amino acid sequences, for example, a PAM120 residue mass table can be used under the settings: gap length penalty=12 and gap penalty=4.

The identity of two amino acid sequences can be determined using the GAP program in the GCG software package, using the Blossom 62 matrix or PAM250 matrix, under the settings: gap weight=12, 10, 8, 6, or 4, and gap length weight=2, 3, or 4.

The transesterification lipase which is an active ingredient of the present enzyme preparation, that is, the present enzyme, may be a part of a larger protein (for example, fusion protein). Examples of the sequence to be added in the fusion protein include a sequence useful for purification such as a sequence of a multiple histidine residue, and an additional sequence ensuring stability during recombinant production.

The present enzyme can be obtained by culturing a producer microorganism for the transesterification lipase (transesterification lipase-producer strain). The transesterification lipase-producer strain may be a wild strain or a mutant strain (a mutant strain can be obtained, for example, by ultraviolet irradiation). A specific example of the transesterification lipase-producer strain is the *Burkholderia ubonensis* DSM 17311 strain (the present enzyme-producer strain). The strain is stored in Leibniz Institut DSMZ (German Collection Microorganisms and Cell Cultures) (Inhoffenstr. 7B, D-38124 Braunschweig, Germany), and can be obtained through predetermined procedures. The mutant strain can be obtained, for example, by irradiation with ultraviolet rays, X rays, γ rays, or the like, or treatment with nitrous acid, hydroxylamine, N-methyl-N'-nitro-N-nitrosoguanidine, or the like. The mutant strain is not limited as long as it produces the present enzyme. Examples of the mutant strain include strains with improved productivity of the present enzyme, strains with reduced productivity of contaminants, strains which are easily cultured, and strains which are easily collected from a culture solution.

Through study by the present inventors, various properties of the lipase of the present invention were determined as follows (for details, see the Examples which will be described later). Therefore, the present enzyme can be specified by the following enzymological properties in addition to its origin. A commercially available kit can be used to measure the lipase activity in the evaluation of the respective enzymological properties (detailed measurement conditions and measurement procedures will be presented in the Examples which will be described later).

(1) Action

The present enzyme is a lipase and catalyzes a transesterification reaction.

(6) Optimum pH

The optimum pH of the present enzyme is about 8. The optimum pH is, for example, determined based on results of measurement in a McIlvaine buffer solution within the pH range of 3 to 8, and in a 0.1M Tris-hydrochloric acid buffer solution (Tris-HCl) within the pH range of 9 to 10.

(3) pH Stability

The present enzyme shows a stable activity at the pH range of 3 to 10. For example, if the pH of the enzyme solution to be treated is within this range, the present enzyme shows 90% or more of the maximum activity after treatment at 30° C. for 1 hour. The pH stability is, for example, determined based on results of measurement in a McIlvaine buffer solution within the pH range of 3 to 8, and in a 0.1M Tris-hydrochloric acid buffer solution (Tris-HCl) within the pH range of 9 to 10.

(4) Optimum Temperature

The optimum temperature of the present enzyme ranges from 40° C. to 70° C.

(5) Temperature Stability

The present enzyme maintains 90% or more activity even when treated in purified water under the condition of 20° C. to 70° C. for 1 hour.

The present enzyme, which is an active ingredient of the present enzyme preparation, catalyzes a transesterification reaction. The transesterification reaction in the present invention refers to a transesterification reaction to bring fatty acids contained in an oil or fat closer to a state of being non-site-specifically bound to the hydroxyl group at position 1, 2, or 3 of glycerol, which is referred to also as non-site-specific transesterification reaction. On the other hand, transesterification reactions specific to the hydroxyl groups at positions 1 and 3 are referred to as 1, 3-position-specific transesterification reactions. The transesterification activity can be measured or evaluated by a method shown in the Examples which will be described below (method for measuring the transesterification activity using a refined palm oil as a substrate, or a method for evaluating the transesterification activity using cacao oil (cacao butter) as a substrate). In the evaluation method using a refined palm oil (fatty acid composition: PPP: about 8%, POP+PPO: about 41%, POO: about 41%, and OOO: about 10%) as a substrate, the refined palm oil contains oleic acid (O) and palmitic acid (P) as constituent fatty acids, the ratios of the fatty acid composition of triglycerides are, roughly, about 8% for PPP, about 41% for POP+PPO, about 41% for POO, and about 10% for OOO, and POP accounts for about 90% of POP+PPO. Thus, tolpalmitin (PPP) is increased mainly by a transesterification reaction. Accordingly, the transesterification activity can be evaluated using an increment of tripalmitin as an index. Cacao oil contains oleic acid, palmitic acid, stearic acid, and the like as constituent fatty acids, and contains, as the main ingredient, a triglyceride having oleic acid bound mainly at position 2. Thus, tripalmitin (PPP) in which palmitic acid is bound to each of positions 1, 2, and 3 is produced only by a transesterification reaction (site-non-specific transesterification reaction) (palmitic acid at position 1 or 3 must be exchanged with oleic acid at position 2, and, when the reaction is caused using a lipase specific to positions 1 and 3, no triglyceride with palmitic acid inserted into position 2 is produced). Therefore, the evaluation method using cacao oil as a substrate can be used to evaluate the transesterification activity using the amount of tripalmitin produced as an index. The transesterification ability can also be evaluated by calculating the transesterification activity per weight, but the transesterification activity per enzyme activity can be calculated to properly evaluate the superiority or inferiority of the transesterification ability (site-non-specific transesterification reactivity).

A representative example of the present enzyme (transesterification lipase including the amino acid sequence of SEQ ID NO: 1 or 2), which is an active ingredient of the present enzyme preparation, causes a fast transesterification reaction and has excellent reaction efficiency, as shown in the Examples which will be described below. Furthermore, it provides less production of diglycerides, when allowed to react with an oil or fat, and causes the transesterification reaction superiorly to the hydrolysis reaction. Therefore, when the present enzyme preparation is used for modifying and improving the physical properties of an oil or fat, a processed product of an oil or fat, or the like (details will be described later), it can be expected not only to shorten the processing time, but also to improve the quality (acquire the desired physical properties) due to the fact that, through the site-non-specific transesterification, the fatty acid composition of the oil or fat is different from that before the treatment (especially, the composition different in fatty acid at position 2), further to improve the yield of triglycerides, and to suppress the production of diglycerides and fatty acid that adversely affect the quality of the oil or fat.

The content of the active ingredient (the present enzyme) in the present enzyme preparation is not particularly limited, and, for example, can be set or adjusted so that the enzyme activity per g of the present enzyme preparation is 1 U to 1000 U, preferably 10 U to 300 U. The enzyme preparation of the present invention is usually provided in a solid form (for example, a granule, powder, or an immobilized enzyme prepared by immobilizing the enzyme on a material capable of immobilizing the enzyme on the surface or inside of a carrier, such as silica, diatomaceous earth or a porous polymer) or in a liquid form. The enzyme preparation may contain an excipient, a buffer agent, a suspending agent, a stabilizer, a preservative, an antiseptic, saline, and the like besides the active ingredient (the present enzyme). As the excipient, lactose, sorbitol, D-mannitol, maltodextrin, white soft sugar, and the like can be used. As the buffer agent, phosphates, citrates, acetates, and the like can be used. As the stabilizer, propylene glycol, ascorbic acid, and the like can be used. As the preservative, phenol, benzalkonium chloride, benzyl alcohol, chlorobutanol, methylparaben, and the like can be used. As the antiseptic, benzalkonium chloride, paraoxybenzoic acid, chlorobutanol, and the like can be used.

2. Method for Manufacturing the Present Enzyme

A further aspect of the present invention provides a method for manufacturing the present enzyme. The manufacture method according to the present invention involves a step (step (1)) of culturing a producer microorganism for the present enzyme and a step (step (2)) of collecting a lipase from a culture solution and/or cell bodies after the culture.

Conditions and methods for culturing cells of are not particularly limited, as long as the inventive enzyme is produced. Thus, methods and culture conditions that are suitable for culturing a microorganism to be used can be set as appropriate, with the proviso that the inventive enzyme is produced. Although the culturing may be by either liquid culture or solid culture, liquid culture is preferably employed. Taking liquid culture as an example, culturing conditions therefor will be described below.

As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of microorganisms to be used, vitamin, amino acid, and the like, may be added to the medium. The medium is cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 20 days (preferably 3 to 10 days). An example of the culture method may include a shake culture method, and an aerobic submerged culture method by using a jar fermenter.

After culturing under the above conditions, the target protein is collected from the culture solution or the cell bodies (step (2)). When it is collected from the culture solution, the present enzyme can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the preset enzyme can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

Also, the present enzyme can easily be prepared by a genetic engineering technique. For example, the present enzyme can be prepared by transforming a suitable host cell (for example, *Escherichia coli*) with a DNA encoding the present enzyme (as examples, a DNA sequence encoding the present enzyme including the amino acid sequence of SEQ ID NO: 1 is shown in SEQ ID NO: 3, and a DNA sequence encoding the present enzyme including the amino acid sequence of SEQ ID NO: 2 is shown in SEQ ID NO: 4) and collecting the protein expressed in the transformant. The collected protein is appropriately purified depending on the purpose. Thus, when the present enzyme is obtained as a recombinant protein, various modifications can be made. For example, a DNA encoding the present enzyme and another appropriate DNA are inserted into the same vector, and a recombinant protein is produced using the vector, so that the present enzyme including the recombinant protein to which any peptide or protein is linked can be obtained. Further, a sugar chain and/or a lipid may be added, or a modification that causes processing at the N-terminus or C-terminus may be performed. The modification as described above enables extraction of recombinant protein, simplification of purification, addition of biological functions, and the like.

Generally, genetic expression and collection of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

The degree of purification of the enzyme is not particularly limited. For example, the enzyme can be purified into a state of having a specific activity of hydrolysis activity of 1 to 100000 (U/μg), preferably a specific activity of 10 to 20000 (U/μg). The final form of the enzyme may be a liquid form or a solid form (including a powder form).

3. Use of the Present Enzyme Preparation/the Present Enzyme (Transesterification Method for Oils and Fats)

A further aspect of the present invention relates to use of the present enzyme preparation/the present enzyme, and provides a transesterification method for oils and fats using the present enzyme preparation or the present enzyme. In the transesterification method of the present invention, a step of allowing the present enzyme preparation or the present enzyme to act on oils and fats is carried out to perform transesterification of the oils and fats, that is, to reorganize (rearrange) constituent fatty acids of triacylglycerol (abbreviated as TG or TAG) in the oils and fats.

Examples of the oils and fats that can be treated by the transesterification method of the present invention can include: vegetable oils and fats such as soybean oil, rapeseed oil, rice oil, corn oil, sunflower oil, cottonseed oil, peanut oil, safflower oil, palm oil, palm soft oil, palm fractionated oil, palm kernel oil, coconut oil, and cacao butter; animal oils and fats such as fish oil, lard, beef tallow, and milk fat, and fractionated oils and hydrogenated oils thereof; and synthetic oils and fats such as trilaurin, triolein, and tripalmitin. The transesterification method of the present invention can be used in transesterification between oils or fats, and also in transesterification between oils or fats and fatty acids or fatty acid esters. Examples of the fatty acids include stearic acid, palmitic acid, lauric acid, arachidic acid, behenic acid, oleic acid, and linoleic acid, and examples of the fatty acid esters include ethyl stearate, ethyl palmitate, ethyl oleate, and ethyl linoleate.

The transesterification method of the present invention involves adding the present enzyme preparation or the present enzyme to an oil or fat to cause a reaction, for example, at 30 to 100° C., preferably at 35 to 80° C. for a predetermined time (for example, 1 to 48 hours). In order to accelerate the reaction, stirring may be performed during the reaction.

The present enzyme preparation or the present enzyme may be subjected to immobilization treatment, and a reaction with the immobilized enzyme may be performed. A batch stirred tank reactor, a flow stirred tank reactor, a packed bed reactor, a fluidized bed reactor, and the like can be used for the reaction with the immobilized enzyme.

The transesterification method of the present invention is useful for modifying and improving the physical properties of oils and fats or processed products of oils and fats (for example, shortening and margarine). For example, the transesterification method of the present invention can be applied for improving spreadability, improving emulsion stability, optimizing a solid fat content (SFC), improving solidification, selectively concentrating specific fatty acids, producing low-trans acid oils and fats or processed products of low-trans acid oils and fats, or the like. The oils and fats or processed products of oils and fats containing the oils and fats obtained by applying the transesterification method of the present invention have improved physical properties as compared with those before treatment, and are of high industrial utility value.

As is clear from the above description, transesterified oils and fats can be manufactured according to the transesterification method of the present invention. That is, the present invention also provides a method for manufacturing a transesterified oil or fat. Typically, the method for manufacturing a transesterified oil or fat according to the present invention involves providing an acceptor substrate (an oil or fat (triglyceride), glycerin fatty acid ester (diglyceride or monoglyceride), or glycerin) and a donor substrate (fatty acid, an ester compound (fatty acid ester or the like), or an oil or fat (which may be the same as the acceptor substrate)) and allowing the present enzyme preparation or the present enzyme to act (that is, an enzymatic reaction in the presence of the acceptor substrate and the donor substrate). The oils and fats, fatty acids, and fatty acid esters used in the acceptor substrate and the donor substrate can be those described above. As the conditions for the enzymatic reaction, the above-mentioned conditions (for example, the reaction is caused under conditions of 30 to 100° C., preferably 35 to 80° C. for a predetermined time (for example, 1 to 48 hours)) can be adopted.

EXAMPLES

1. Preparation of the Present Lipase

A producer strain for the present enzyme was inoculated into a preculture medium after sterilization and cultured at 30° C. for 3 days to obtain a preculture solution.
<Preculture Medium>
Yeast extract (manufactured by Becton Dickinson Co., Ltd.): 0.5%
Bacto Peptone (manufactured by Becton Dickinson Co., Ltd.): 1.0%
Sodium chloride (manufactured by Fujifilm Wako Pure Chemical Corporation): 0.5%
pH 7.2
The preculture solution was added to a main culture medium after steam sterilization, and subjected to shaking culture at 30° C. for 3 days to obtain a culture solution.

<Main Culture Medium>
Soybean oil: 2.0%
Peptone: 0.5% (manufactured by Difco)
Meat extract: 0.3% (manufactured by Difco)
Potassium dihydrogen phosphate: 0.1%
Magnesium sulfate heptahydrate: 0.02%
Iron(II) sulfate heptahydrate: 0.001%
Adekanol LG-126 (manufactured by ADEKA Corporation): 0.2%

The obtained culture solution was centrifuged to collect a culture supernatant. The culture supernatant was subjected to diatomaceous earth filtration to obtain a clear solution. The clear solution was concentrated and desalted by ultrafiltration, and the resulting desalted solution was freeze-dried to obtain crude purified enzyme powder (the present lipase). The molecular weight of the present lipase, when confirmed by SDS-PAGE, was found to be about 33 kDa.

A lipase derived from *Rhizopus oryzae* (lipase DF), a lipase derived from *Pseudomonas fluorescens* (lipase AK), a lipase derived from *Burkholderia cepacia* (lipase PS), and a lipase derived from *Penicillium camembertii* (lipase G) were each obtained from Amano Enzyme Inc.

2. Study of Transesterification Activity Per Hydrolysis Activity (1) Evaluation Method A refined palm oil (Imagine, Inc., fatty acid composition: PPP: about 8%, POP: about 41%, POO: about 41%, and OOO: about 10%) is dissolved at 60° C. immediately before use. The enzyme to be used (0.2 g) is weighed into a 100-mL Erlenmeyer flask with a screw cap. The dissolved refined palm oil (20 mL) is added. The time point of addition is t=0. The mixture is shaken at 60° C. and 160 rpm. Thirty (30) minutes, 60 minutes, and 120 minutes after the start of shaking, sampling is carried out (10 μL). The sample is dissolved in 1 mL of Hexane. The sample passing through a 0.45-μm filter is subjected to gas chromatography (GC) analysis to measure the amount of tripalmitin (PPP) produced. The ratio (%) of the PPP amount (PPP) to the total amount of triacylglycerol (Total TAG) in the refined palm oil is calculated, and a difference between before and after the reaction is defined as PPP increment (%). The transesterification activity per hydrolysis activity was evaluated by comparing numerical values obtained by multiplying the hydrolysis activity ratios of the respective enzymes, when the hydrolysis activity of the lipase BU is 1, by the PPP increments of the respective enzymes. The hydrolytic activity was measured using Lipase Kit S. To 250 μL of an undiluted color developing solution, 250 μL of the buffer solution included in the kit and 2000 μL of purified water were added to make a color developing solution. Into a test tube, 1 mL of the color developing solution, 50 μL of a diluted solution obtained by diluting the 5 mg/mL enzyme solution to an appropriate concentration, and 20 μL of an esterase inhibitor are charged, and kept warm at 30° C. for 5 minutes. Then, 100 μL of a substrate solution is added, and the mixture is further allowed to react at 30° C. for 30 minutes. Thereafter, 2 mL of a reaction stop solution is charged in the reaction product. The total amount of the sample after stop of the reaction is transferred to a 15-mL tube, and centrifuged at 8000 g for 1 minute. Thereafter, a supernatant is collected, and the absorbance is measured at 412 nm. A product obtained by adding the enzyme solution and the esterase inhibitor after addition of the reaction stop solution was used as a blank, and calculation was performed based on the following equation:

$$U/mg = (A412\ sample - A412\ blank) \times 1/0.05 \times 1/5 \times n$$

(wherein A412 sample is the absorbance at 412 nm of the sample, A412 blank is the absorbance at 412 nm of the blank, 0.05 is the amount (mL) of the sample added, 5 is the concentration of the enzyme solution (5 mg/mL), and n is the dilution rate of the enzyme solution.)

GC Analysis Conditions
Column: DB-1ht (5 m)
Detector: FID
Oven temperature: initially held at 120° C. for 1 minute→increased at 25° C./min (up to 150° C.)→increased at 30° C./min (up to 260° C.)→increased at 20° C./min (up to 370° C.)→held at 370° C. for 3 minutes
Vaporization chamber temperature: 370° C.
Detector temperature: 370° C.
Injection volume: 1 μL
Column inlet pressure: 100 kpa (only during injection)
Carrier gas: He
Split ratio: 1:50

(2) Results

Figure 1:
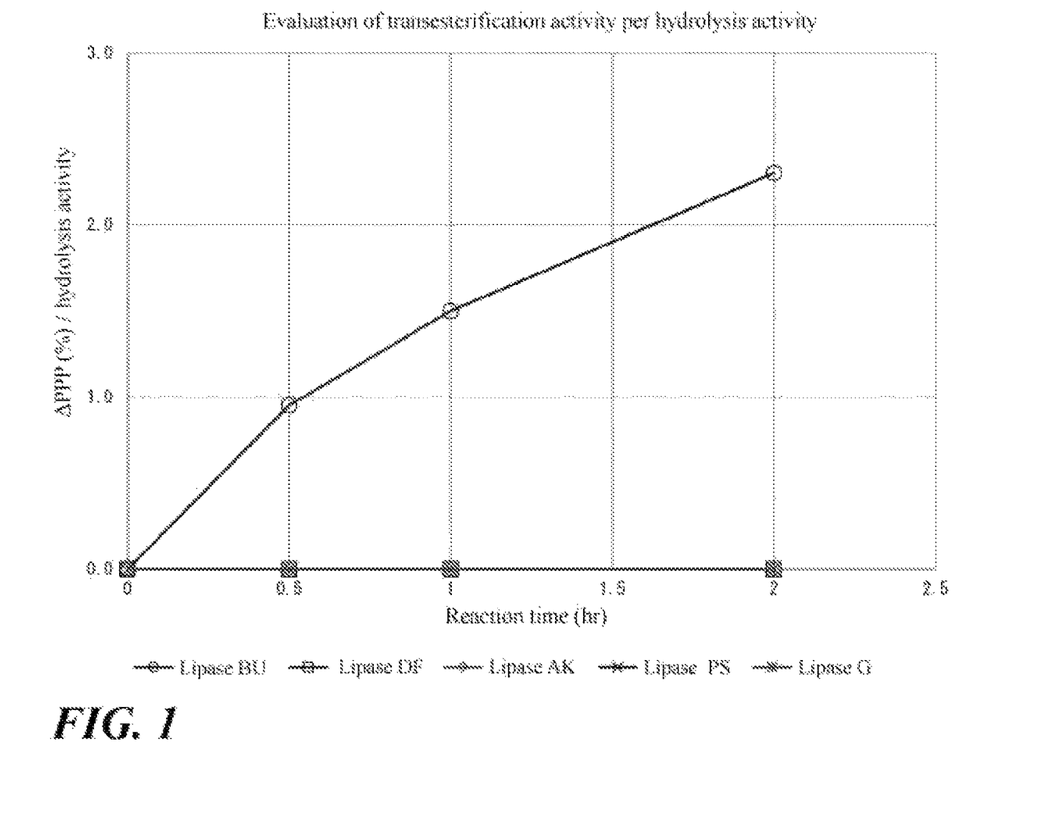
FIG. 1 Study of transesterification activity. The present lipase was compared, in terms of the transesterification activity, with various lipases (a lipase derived from *Rhizopus oryzae* (lipase DF), a lipase derived from *Pseudomonas fluorescens* (lipase AK), a lipase derived from *Burkholderia cepacia* (lipase PS), and a lipase derived from *Penicillium camembertii* (lipase G)).

The present lipase was found to have a higher transesterification activity per hydrolytic activity than those of the other lipases (FIG. 1 and Table 1).

TABLE 1

|  | Reaction time (hr) | | |
| --- | --- | --- | --- |
|  | 0.5 | 1 | 2 |
| The present lipase | 1.0 | 1.5 | 2.3 |
| Lipase DF | 0 | 0 | 0 |
| Lipase AK | 0 | 0 | 0 |
| Lipase PS | 0 | 0 | 0 |
| Lipase G | 0 | 0 | 0 |

Summary of evaluation results (comparison in PPP increment (%)/hydrolysis activity)

3. Study of Transesterification Activity Per Enzyme Activity (1) Enzyme Activity Evaluation Method (GC)

To a screw vial, 2.5 mL of triolein (Tokyo Chemical Industry Co., Ltd.) is added. A certain amount of powder of each of the lipases is weighed, added, and preheated while stirring in an oil bath at 60° C. Added is 3.0 mL of methyl palmitate (Tokyo Chemical Industry Co., Ltd.), and the reaction is started at 60° C. Sampling is carried out over time (30 μL sample/1.0 mL Hexane), and the amount of the methyl oleate produced is measured by gas chromatography (GC). The amount of the enzyme that produces 1 μmol of methyl oleate in 1 minute under the reaction conditions is defined as 1 U, and calculation is performed based on the following equation:

$$\text{Enzyme activity (U/g)} = A/a \times 33 \times (1/T) \times (1/G) \times 5.5$$

(A: area of methyl oleate, a: slope of a calibration curve, 1/T: conversion to 1-minute reaction time, and 1/G: conversion to 1-g sample)

GC Analysis Conditions
Column: DB-1HT (length: 5 m, film thickness: 0.1 μm, and inner diameter: 0.25 mm)
Detector: FID
Oven temperature: initial: 50° C., increased at 40° C./min, and final: 370° C.
Vaporization chamber temperature: 370° C.
Detector temperature: 370° C.
Injection volume: 1 μL
Column inlet pressure: 100 kPa
Carrier gas: He
Split ratio: 1:50

(2) Transesterification Activity Evaluation Method (GC)

The enzyme solution corresponding to 3 U of the enzyme activity was freeze-dried, 3 mL of cacao oil and 6 μL of ultrapure water were added. The reaction was started at 60° C. with stirring. Sampling was carried out 1 day and 4 days after the reaction, and the proportion of tripalmitin (PPP) as an index was measured by GC.

GC Analysis Conditions

Column: DB-1HT (length: 5 m, film thickness: 0.1 μm, and inner diameter: 0.25 mm)

Detector: FID

Column temperature: 120° C. for 4 minutes→increased up to 150° C. (20° C./min)→increase up to 315° C. (30° C./min)→315° C. for 3 minutes→increased up to 325° C. (1.5° C./min)→increased up to 370° C. (30° C./min)→370° C. for 2 minutes Carrier gas: He Split ratio: 50:1

Analysis: PPP proportion was calculated from total peak area (3) Results

The present lipase was found to have a higher transesterification activity per enzyme activity than those of the other lipases (Table 2).

TABLE 2

| | Amount (%) of PPP produced | |
|---|---|---|
| Enzyme sample | After 1 day | After 4 days |
| Lipase PS | 0.7 | 2.1 |
| The present lipase | 2.1 | 2.3 |
| Lipozyme TLIM | 0.6 | 1.8 |

Amount of enzyme added and PPP increment of each sample

4. Study of Change in Oil or Fat Composition (1) Evaluation Method

A refined palm oil (Imagine, Inc., fatty acid composition: PPP: 8%, POP: 41%, POO: 41%, and OOO: 10%) is dissolved at 60° C. immediately before use. One (1) g of the enzyme to be used is weighed into a 100-mL Erlenmeyer flask with a screw cap. The dissolved refined palm oil (20 mL) is added. The time point of addition is t=0. The mixture is shaken at 60° C. and 160 rpm. One hundred and twenty (120) minutes after the start of shaking, sampling is carried out (10 μL). The sample is dissolved in 1 mL of Hexane. The sample passing through a 0.45 μm filter was subjected to gas chromatography (GC) analysis to measure the ratios (%) of triglycerides (TG), diglycerides (DG), monoglycerides (MG), and free fatty acids (FFA), thereby confirming a change in oil or fat composition. In this evaluation, the present lipase (immobilized) obtained by immobilizing the present lipase on diatomaceous earth in accordance with a conventional method was used, and compared with a commercially available immobilized lipase derived from *Thermomyces lanuginosus* (Comparative Product 1).

GC Analysis Conditions

Column: DB-1ht (5 m)

Detector: FID

Oven temperature: initially held at 120° C. for 1 minute→increased at 25° C./min (up to 150° C.)→increased at 30° C./min (up to 260° C.)→increased at 20° C./min (up to 370° C.)→held at 370° C. for 3 minutes Vaporization chamber temperature: 370° C.

Detector temperature: 370° C.

Injection volume: 1 μL

Column inlet pressure: 100 kpa (only during injection)

Carrier gas: He

Split ratio: 1:50

(2) Results

The present lipase (immobilized) was found to have a higher ratio of triglycerides than that of Comparative Product 1, to provide less production of by-products partial glycerides (diglycerides and monoglycerides) and free fatty acids, and thus to be industrially useful (Table 3).

TABLE 3

| Enzyme | TG | DG | MG | FFA |
|---|---|---|---|---|
| Comparative Product 1 | 86 | 9 | 1 | 4 |
| The present lipase (immobilized) | 93 | 6 | 0 | 1 |

Comparison in oil and fat composition (ratios (%) of triglycerides (TG), diglycerides (DG), monoglycerides (MG), and free fatty acids (FFA))

As a further study, the present lipase (immobilized) and two types of immobilized enzymes for comparison were used and allowed to react in an oil or fat. For comparison, a commercially available immobilized lipase derived from *Thermomyces lanuginosus* (Comparative Product 1) and a commercially available immobilized lipase derived from *Rhizomucor miehei* (Comparative Product 2) were used. According to the method described in (1) above, a test section in which 2.0 g of each of the enzymes was added to 20 mL of a refined palm oil and a test section in which no enzyme was added were provided as the reaction systems. A sample was collected 1 hour after the start of the reaction and analyzed under the conditions described in the "GC analysis conditions" above.

As a result of the analysis, the present lipase had a lower ability to generate DG and FFA than that of the comparative products. Thus, it is presumed that the transesterification reaction mainly occurs rather than the hydrolysis reaction. Furthermore, the present lipase had a large increase in ratio of tripalmitin (PPP) in TG compared to the enzymes for comparison, and thus can be said to have an excellent ability to convert POP, POO, and OOO into PPP, and to be industrially useful (Table 4).

TABLE 4

| | Oil or fat composition (%) | | | | Increment (%) of ratio |
|---|---|---|---|---|---|
| Enzyme | TG | DG | MG | FFA | of PPP in TG |
| The present lipase (immobilized) | 95.1 | 4.9 | 0 | 0 | 1.9 |
| Comparative Product 1 | 92.5 | 7.2 | 0 | 0.3 | 0.9 |
| Comparative product 2 | 86.4 | 12.2 | 0 | 1.4 | −0.5 |

Oil or fat composition (%): existence ratios (%) of triglycerides (TG), diglycerides (DG), monoglycerides (MG), free fatty acids (FFA), and PPP when the total amount of TG, DG, MG, and FFA is 100%

Increment (%) of ratio of PPP in TG: Increment of ratio (%) of tripalmitin (PPP) in triglyceride (TG) relative to that when no enzyme was added ((ratio of PPP in TG when enzyme was added)−(ratio of PPP in TG when no enzyme was added))

5. Confirmation of Enzymatic Properties of the Present Lipase 5-1. Optimum pH (1) Method A McIlvaine buffer (pH 3, 4, 5, 6, 7, or 8) and 0.1 mol/L Tris-HCl (p 9 and 9.5) are prepared. The activity at each pH was measured using Lipase Kit S. To 250 μL of an undiluted color developing solution, 2250 μL of the buffer used to make a color developing solution. Into a test tube, 1 mL of the color developing solution, 50 μL of the enzyme solution diluted to an appropriate concentration, and 20 μL of an esterase inhibitor are charged, and kept warm at 30° C. for 5 minutes. Then, 100 μL of a substrate solution is added, and the mixture is further allowed to react at 30° C. for 30 minutes. Thereafter, 2 mL of a reaction stop solution is charged in the reaction product. The total amount of the sample after stop of the reaction is transferred to a 15-mL tube, and centrifuged at 8000 g for 1 minute. Thereafter, a supernatant is collected, and the absorbance is measured at 412 nm. The optimum pH was evaluated based on the relative activity when the activity of the sample in which the actually measured pH value of the reaction solution was 7.9 (sample using the McIlvaine buffer having a pH of 8.0) was 100%. Note that a product obtained by adding the enzyme solution and the esterase inhibitor after addition of the reaction stop solution was used as a blank.

(2) Results

Figure 2:
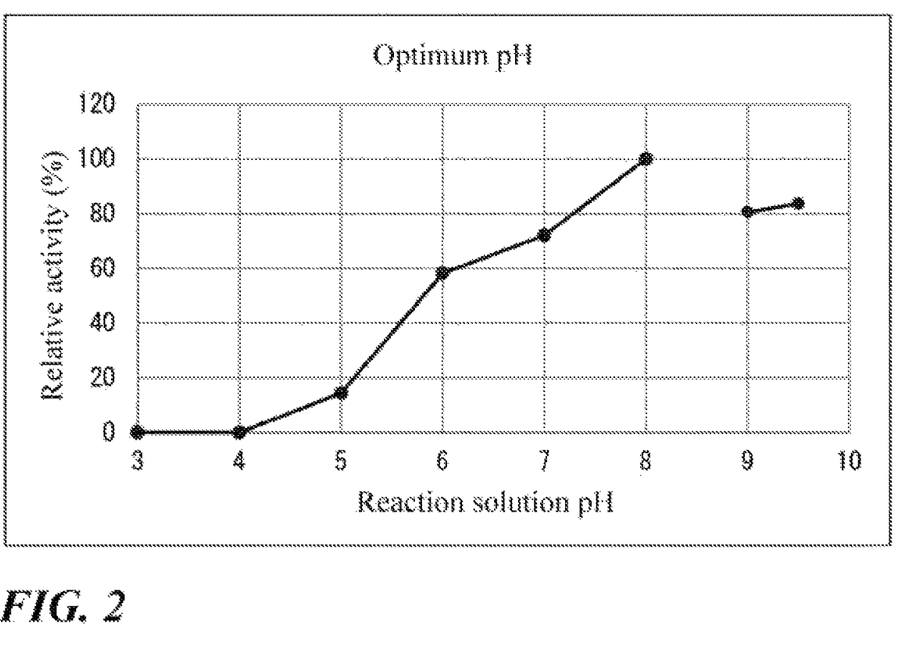
FIG. 2 An optimal pH of the present lipase.

The optimum pH of the present lipase was found to be about 8 (FIG. 2).

5-2. pH Stability (1) Method

A McIlvaine buffer (pH 3, 4, 5, 6, 7, or 8) and 0.1 mol/L Tris-HCl (pH 9 and 10) are prepared. A 15 mg/mL enzyme solution is adjusted using the buffer, and treated at 30° C. for 1 hour. Then, an equal volume of the buffer solution included in Lipase Kit S was added to the treated enzyme solution, and the solution mixture was mixed to prepare a treated sample. The activity of the treated sample was measured using Lipase Kit S. Into a test tube, 1 mL of the color developing solution, 50 μL of the treated sample diluted to an appropriate concentration, and 20 μL of an esterase inhibitor are charged, and kept warm at 30° C. for 5 minutes. Then, 100 μL of a substrate solution is added, and the mixture is further allowed to react at 30° C. for 30 minutes. Thereafter, 2 mL of a reaction stop solution is charged in the reaction product. The total amount of the sample after stop of the reaction is transferred to a 15-mL tube, and centrifuged at 8000 g for 1 minute. Thereafter, a supernatant is collected, and the absorbance is measured at 412 nm. The pH stability was evaluated as a relative activity when the activity of the sample in which the actually measured pH value of the enzyme solution treated at 30° C. for 1 hour was 3.1 (sample using the McIlvaine buffer having a pH of 3.0) was 100%. Note that a product obtained by adding the enzyme solution and the esterase inhibitor after addition of the reaction stop solution was used as a blank.

(2) Results

Figure 3:
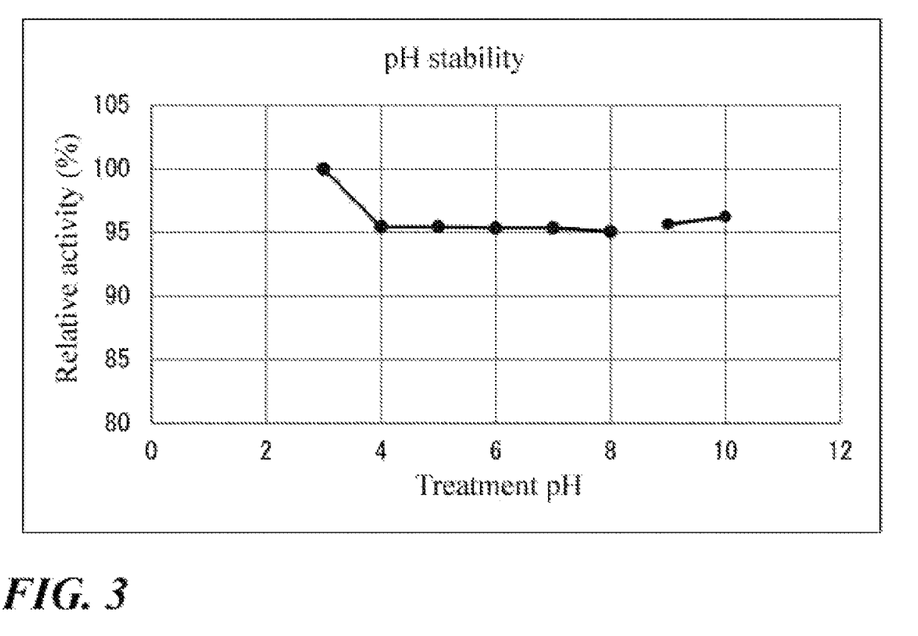
FIG. 3 pH stability of the present lipase.

The present lipase was found to be stable at a pH of 3 to 10 (FIG. 3).

5-3. Optimum Temperature (1) Method

The activity at each temperature was measured using Lipase Kit S. Into a test tube, 1 mL of the color developing solution, 50 μL of the enzyme solution diluted to an appropriate concentration, and 20 μL of an esterase inhibitor are charged, and kept warm at each temperature (20, 30, 40, 50, 60, and 70° C.) for 5 minutes. Then, 100 μL of a substrate solution is added, and the mixture is further allowed to react for 30 minutes. Thereafter, 2 mL of a reaction stop solution is charged in the reaction product. The total amount of the sample after stop of the reaction is transferred to a 15-mL tube, and centrifuged at 8000 g for 1 minute. Thereafter, a supernatant is collected, and the absorbance is measured at 412 nm. The optimum temperature was evaluated based on the relative activity when the activity at 40° C. was 100%. Note that a product obtained by adding the enzyme solution and the esterase inhibitor after addition of the reaction stop solution was used as a blank.

(2) Results

Figure 4:
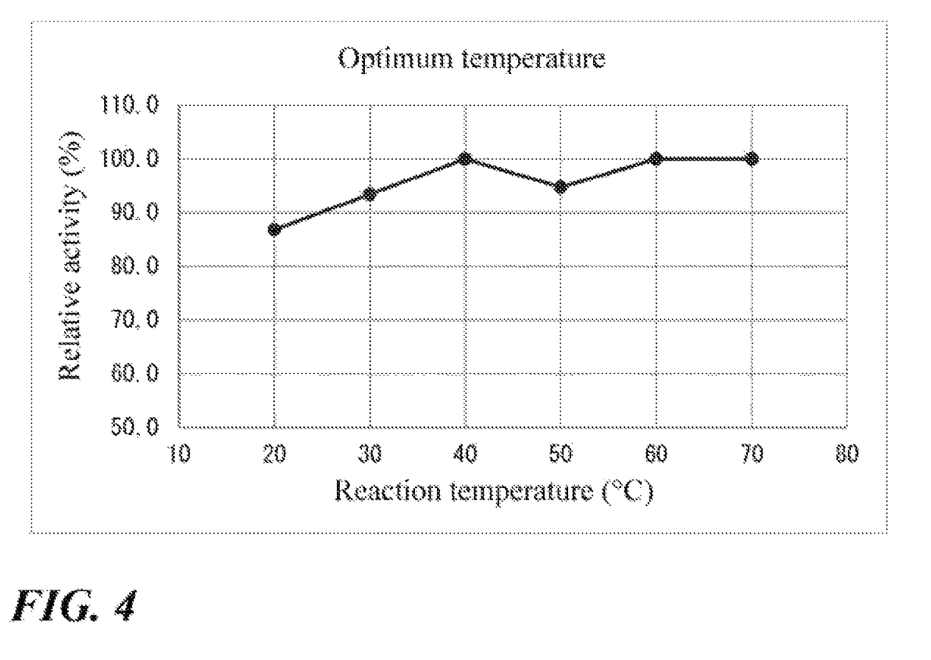
FIG. 4 An optimum temperature of the present lipase.

The optimum temperature of the present lipase was found to range from 40 to 70° C. (FIG. 4).

5-4. Temperature Stability (1) Method

The enzyme powder is dissolved in purified water to attain a concentration of 5 mg/mL, and then treated at each temperature for 1 hour. The activity of the treated sample was measured using Lipase Kit S. Into a test tube, 1 mL of the color developing solution, 50 μL of the treated sample diluted to an appropriate concentration, and 20 μL of an esterase inhibitor are put, and kept warm at 30° C. for 5 minutes. Then, 100 μL of a substrate solution is added, and the mixture is further allowed to react at 30° C. for 30 minutes. Thereafter, 2 mL of a reaction stop solution is charged in the solution. The total amount of the sample after stop of the reaction is transferred to a 15-mL tube, and centrifuged at 8000 g for 1 minute. Thereafter, a supernatant is collected, and the absorbance is measured at 412 nm. The temperature stability was evaluated based on the relative activity when the activity of the sample treated at 30° C. for 1 hour was 100%. Note that a product obtained by adding the enzyme solution and the esterase inhibitor after addition of the reaction stop solution was used as a blank.

(2) Results

Figure 5:
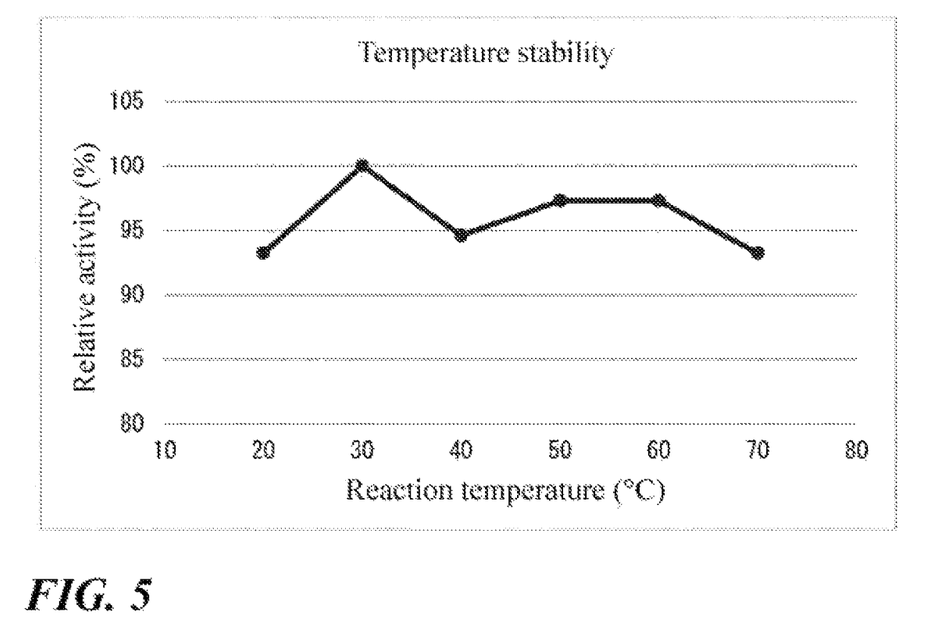
FIG. 5 Temperature stability of the present lipase.

The present lipase was found to be stable at 20 to 70° C. (FIG. 5).

6. Confirmation of Sequence Information

The amino acid sequences of the present lipase extracted by genome analysis and the base sequences encoding the amino acid sequences are shown in the sequence listing. The correspondence between the sequence numbers and the sequences is as follows.

SEQ ID NO: 1: amino acid sequence (including a signal peptide)
SEQ ID NO: 2: amino acid sequence (mature form)
SEQ ID NO: 3: base sequence (including signal sequence)
SEQ ID NO: 4: base sequence (mature form)

INDUSTRIAL APPLICABILITY

The enzyme preparation of the present invention is particularly suitable for use in food applications. It is used, for example, in modifying edible oils and fats such as margarine and shortening. It is also expected to be used for the manufacture of various transesterified oils and fats.

The present invention is not limited to the description of the embodiments and examples of the present invention at all. Various modifications that can be easily achieved by those skilled in the art without departing from the claims also fall within the scope of the present invention. The contents of the articles, patent laid-open publications, patent publications, and the like specified herein shall be cited by incorporation in their entity.

[Sequence Listing]

The invention claimed is:

1. A method for manufacturing a non-site-specific transesterified oil or fat, comprising:
an enzymatic reaction with a lipase comprising an amino acid sequence having 90% or more identity with the amino acid sequence of SEQ ID NO: 1 or 2 in the presence of an acceptor substrate and a donor substrate, wherein the acceptor substrate is a first oil or fat, glycerin fatty acid ester, or glycerin, and the donor substrate is a fatty acid, an ester compound, or a second oil or fat.

2. The method according to claim 1,
wherein the acceptor substrate is the first oil or fat, glycerin fatty acid ester, or glycerin, and
wherein the donor substrate is a fatty acid, an ester compound, or a second oil or fat.

3. The method according to claim 1, wherein
the lipase comprises an amino acid sequence having 93% or more identity with the amino acid sequence of SEQ ID NO: 1 or 2.

4. The method according to claim 1, wherein
the lipase comprises an amino acid sequence having 95% or more identity with the amino acid sequence of SEQ ID NO: 1 or 2.

5. A method for manufacturing a non-site-specific transesterified oil or fat, comprising:
an enzymatic reaction with an enzyme preparation that comprises a lipase comprising an amino acid sequence having 90% or more identity with an amino acid sequence of SEQ ID NO: 1 or 2 in the presence of an acceptor substrate and a donor substrate,
wherein the acceptor substrate is a first oil or fat, glycerin fatty acid ester, or glycerin, and the donor substrate is a fatty acid, an ester compound, or a second oil or fat.

6. The method according to claim 3,
wherein the acceptor substrate is the first oil or fat, glycerin fatty acid ester, or glycerin, and
wherein the donor substrate is a fatty acid, an ester compound, or the second oil or fat.

7. The method according to claim 2,
wherein the first oil or fat is same as the second oil or fat.

8. The method according to claim 2,
wherein the first oil or fat is different from the second oil or fat.

* * * * *